United States Patent [19]

Shephard

[11] 4,189,430
[45] Feb. 19, 1980

[54] EPOXIDE PROCESS
[75] Inventor: Kenneth P. Shephard, Portage, Mich.
[73] Assignee: The Upjohn Company, Kalamazoo, Mich.
[21] Appl. No.: 929,506
[22] Filed: Jul. 31, 1978
[51] Int. Cl.² ........................... C07J 21/00; C07J 5/00
[52] U.S. Cl. ........................ 260/239.55 R; 260/397.45
[58] Field of Search ....... Machine Searched Steroids; 260/239.55 R, 397.45

[56] References Cited

U.S. PATENT DOCUMENTS

| | | | |
|---|---|---|---|
| 3,281,415 | 10/1966 | Schneider et al. | 260/397.45 |
| 3,375,261 | 3/1968 | Arth et al. | 260/397.45 |
| 3,444,216 | 5/1969 | Parikh et al. | 260/397.45 |
| 3,725,392 | 4/1973 | Beal et al. | 260/397.45 |
| 3,876,633 | 4/1975 | Loken | 260/239.55 R |

FOREIGN PATENT DOCUMENTS

| | | | |
|---|---|---|---|
| 1297604 | 6/1969 | Fed. Rep. of Germany | 260/397.45 |
| 1301999 | 8/1970 | Fed. Rep. of Germany | 260/397.45 |

*Primary Examiner*—Elbert L. Roberts
*Attorney, Agent, or Firm*—Bruce Stein

[57] ABSTRACT

11$\beta$,21-Dihydroxypregna-1,4,17(20)-triene-3-one 21-acetate (0) is epoxidized, followed by ring opening and hydrolysis to give 11$\beta$,20,21-trihydroxypregna-1,4,16-triene-3-one 21-acetate (III), an intermediate in the synthesis of betamethasone, in improved yields.

23 Claims, No Drawings

EPOXIDE PROCESS

BACKGROUND OF THE INVENTION

U.S. Pat. No. 3,725,392 (Beal) discloses a process to produce various 9α-fluoro-16β-alkylprednisolones including 9α-fluoro-16β-methylprednisolone (betamethasone) which are known to be highly active anti-inflammatory agents. The prednisolone type steroids have a $\Delta^{1,4}$-3-keto A ring. Beal discloses that the process can be performed on a prednisolone type compound ($\Delta^{1,4}$-3-keto) or a cortisone type ($\Delta^{4}$-3-keto) and the $\Delta^{1}$ double bond put in later. The first 2 steps of Beal are the transformation of a 11β,21-dihydroxypregna-4,17(20)-dien-3-one to a 11β,20,21-trihydroxypregna-4,16-dien-3-one. Example 1 of Beal discloses that starting with 165.2 g. (0.5 mole) of the $\Delta^{17(20)}$ compound, 51.1 g. (0.15 moles) of the $\Delta^{16}$-21-ol is obtained, a 30% chemical yield. Beal's process involves photosensitized oxygenation followed by reduction. The process of the present invention accomplishes the transformation of a $\Delta^{17(20)}$ steroid to a $\Delta^{16}$ steroid surprisingly and unexpectedly in about 89% yield, an almost 60% yield increase over Beal.

U.S. Pat. No. 3,281,415 discloses the transformation of a 17(20)-olefinic steroid to the corresponding $\Delta^{16}$-20-keto steroid. Claim 20 claims a process of producing compounds of formulas (II and III) of the present invention. However, claim 20 of U.S. Pat. No. 3,281,415 claims photosensitized oxygenation whereas the process of the present invention uses a peracid and proceeds via an epoxide not a hydroperoxide. In column 30, at line 8 "11β,20α,21-trihydroxy-1,4,16-pregnatrien-3-one 21-acetate" is disclosed as the starting material to prepare the corresponding 20-keto compound. However, the patent does not teach how to prepare this compound.

German Pat. No. 1,301,999 discloses a process for transforming a 17α,20α-epoxypregnane to a $\Delta^{16}$-21-ol in about 90% yield by use of 1.82 equivalents of hydrogen bromide. The 10% impurity is the 17β-bromide. The process of the present invention surprisingly and unexpectedly requires only about 0.03–0.05 equivalents of hydrogen bromide and produces less than 1% of the 17β-bromide.

German Pat. No. 1,297,604 discloses a process for transforming a $\Delta^{17(20)}$-pregnane into a $\Delta^{16}$-21-ol by peracid oxidation of the $\Delta^{17(20)}$-pregnane to the corresponding 17α,20α-epoxide which is then reacted with hydrogen iodide to form a 17β-iodide which is then transformed to the $\Delta^{16}$-21-ol. The process of the present invention involves peracid oxidation to form an epoxide, however the epoxide when reacted with the acid surprisingly and unexpectedly forms the $\Delta^{16}$-20-ol directly without forming a 17β-halide.

SUMMARY OF THE INVENTION

Disclosed is a compound of the formula:

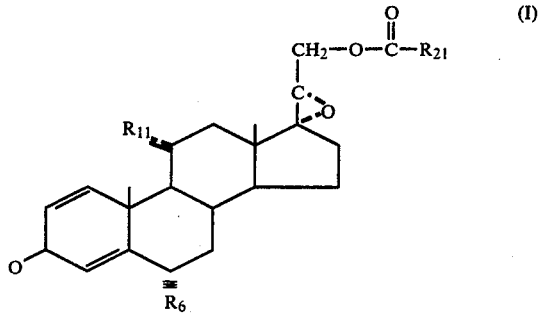

Also disclosed is a compound of the formula:

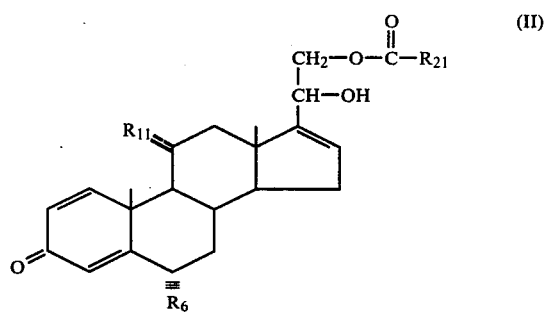

Disclosed is a process for the preparation of a compound of the formula:

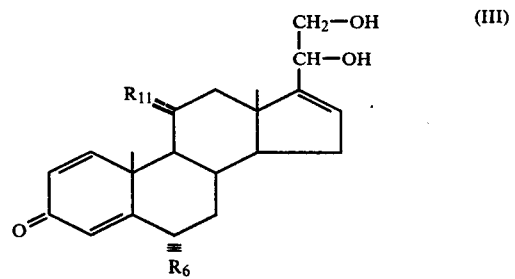

which comprises (1) oxidizing an olefin of the formula:

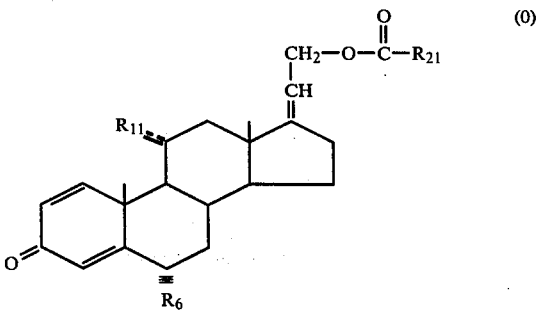

with a peracid to form an epoxide of the formula:

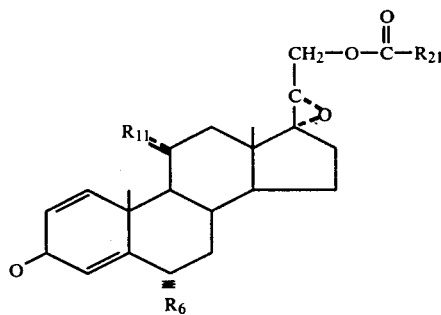

(2) opening of the epoxide ring with an acid selected from the group consisting of hydrochloric and hydrobromic to form a compound of the formula:

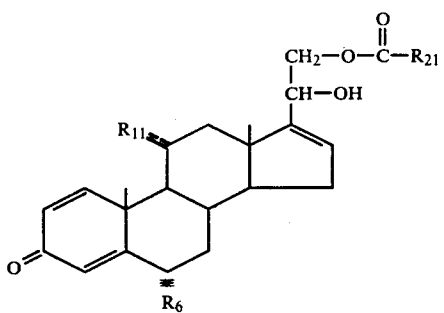

and
(3) hydrolyzing with a base.

Disclosed is a process for the preparation of an epoxide of formula (I) which comprises oxidizing an olefin of the formula (0) with a peracid.

Also disclosed is a process for the preparation of a compound of formula (II) which comprises opening of the epoxide ring of an epoxide of formula (I) with an acid selected from the group consisting of hydrochloric and hydrobromic.

Further disclosed is a process for the preparation of a compound of formula (III) which comprises hydrolyzing a compound of the formula (II) with a base.

Further disclosed is a process for the preparation of a compound of formula (II) which comprises (1) oxidizing an olefin of formula (0) with a peracid and (2) opening of the epoxide ring with an acid selected from the group consisting of hydrochloric and hydrobromic.

Also disclosed is a process for the preparation of a compound of formula (III) which comprises (1) opening of the epoxide ring of a compound of formula (I) with an acid selected from the group consisting of hydrochloric and hydrobromic and (2) hydrolyzing with a base.

DETAILED DESCRIPTION OF THE INVENTION

The process of the present invention (see Chart A) is a process for the preparation of a compound of formula (III) which comprises (1) oxidizing an olefin of formula (0) with a peracid to form an epoxide (I), (2) opening the epoxide ring with an acid selected from the group consisting of hydrochloric and hydrobromic acid to form a compound of formula (II) and (3) hydrolyzing with a base.

The peracid oxidation of the 17(20) olefin to the 17α,20α-epoxide can be performed with virtually any peracid. It is preferred the peracid be selected from the group consisting of peracetic, perpropionic, perbenzoic and m-chloroperbenzoic. It is most preferred the peracid be peracetic acid. Peracids (especially peracetic) are commercially available or may be readily prepared from the corresponding acid by means well known to those skilled in the art. At least 1.0 equivalent of the peracid is required and one may use as much as 5.0 equivalents. It is preferred that about 1.5 equivalents of the peracid be used. The peracid oxidation can be performed in most non-polar solvents such as methylene chloride, chloroform, toluene, cyclohexane and SSB. The reaction can be performed in the temperature range of about 0° to the reflux temperature of the particular solvent utilized. It is preferred that the reaction temperature be 20°–25°. At colder temperatures the reaction proceeds slowly and at higher temperatures the reaction proceeds faster but heating is required. At 20°–25° the reaction is complete after stirring overnight. When the oxidation reaction is complete as measured by TLC, the excess peracid is destroyed by an inorganic reducing agent such as sodium thiosulfate or sodium sulfite.

CHART A

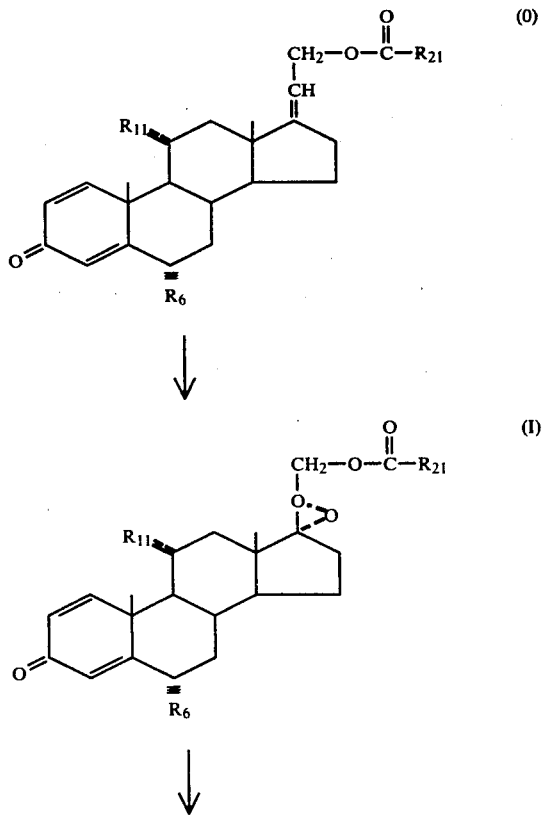

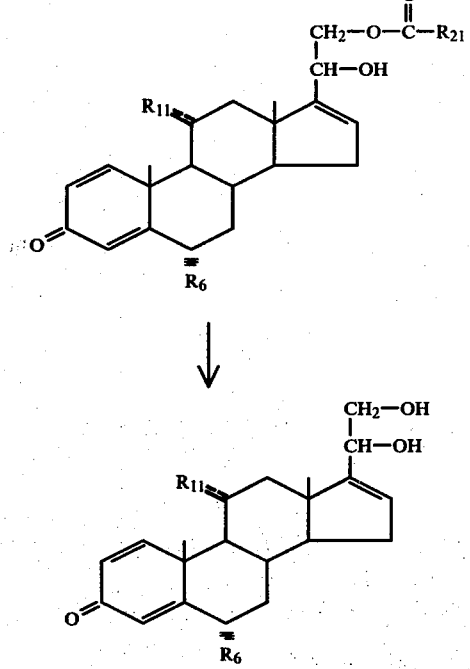

The epoxide formed is then opened by reaction with either hydrochloric or hydrobromic acid. Hydrobromic is preferred. The preferred amount is 0.03–0.05 equivalents. It should be noted German Pat. No. 1,301,999 utilized 1.82 equivalents of acid to open the epoxide. More acid can be used in the present invention but as more acid is utilized hydrolysis of the $C_{21}$ ester occurs as well as formation of the 17β-halide. The epoxide opening is best performed in polar oxygenated solvents such as THF, dioxane or diethyl ether; THF is the preferred solvent. It is also preferable that the polar oxygenated solvent be dry as less acid is then required. This reaction is preferably performed at 20°–25° although lower or higher temperatures will also work. The acid is best slowly added to the epoxide to avoid side reactions.

The hydrolysis is performed utilizing a strong base such as sodium hydroxide, potassium hydroxide, methoxide, ethoxide, sodium carbonate, potassium carbonate, sodium bicarbonate and potassium bicarbonate. The hydrolysis reaction is performed in polar solvents such as acetone and/or alcohol. At 20°–25° the reaction is complete in about 30 minutes. For weaker bases the reaction time will be a little longer.

The product of the reactions of the present invention is the 11β,20,21-trihydroxypregna-1,4,16-trien-3-one (III). This compound is the compound of formula III of U.S. Pat. No. 3,725,392 where there is a double bond between carbon atoms 1 and 2, see column 2, lines 27 and 28. Therefore, the compound of formula (III) is an important intermediate in the synthesis of 9α-fluoro-16β-methylprednisolone (betamethasone) an important anti-inflammatory steroid. Compounds (I) and (II) are therefore important intermediates in the synthesis of betamethasone.

The definitions and explanations below are for the terms as used throughout the entire patent application including both the specification and claims.

All temperatures are in degrees Centigrade.

TLC refers to thin-layer chromatography.
THF refers to tetrahydrofuran.
SSB refers to a mixture of isomeric hexanes.
Saline refers to an aqueous saturated sodium chloride solution.

$[\alpha]_D^{25}$ refers to the angle of rotation of plane polarized light (specific optical rotation) at 25° with the sodium D line (5893A).

$R_6$ is a hydrogen or fluorine atom or methyl group.
$R_{11}$ is a β-hydroxyl or oxo group with the proviso that when $R_{11}$ is β-hydroxyl ≡≡≡ is a single bond and when $R_{11}$ is oxo ≡≡≡ is a double bond.

$R_{21}$ is alkyl of 1 thru 3 carbon atoms, phenyl substituted with 0 thru 3 substituents which may be the same or different and are selected from the group consisting of a fluorine or chlorine atom or methyl, methoxy or nitro group.

≡≡≡ is a single or double bond and when $R_{11}$ is β-hydroxyl ≡≡≡ is a single bond and when $R_{11}$ is oxo ≡≡≡ is a double bond.

The terms 11β,20,21-trihydroxypregna-1,4,16-trien-3-one 21-acetate (II) and 11β,20,21-trihydroxypregna-1,4,16-trien-3-one (III) include both α and β epimers at $C_{20}$. The process of examples 1 and 4 forms both α and β epimers though the ratio of α:β epimers is about 99:1.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1

11β,21-Dihydroxy-17α,20α-epoxypregna-1,4-dien-3-one 21-acetate (I)

11β,21-Dihydroxypregna-1,4,17(20)-trien-3-one 21-acetate (O, U.S. Pat. No. 2,842,569, 79.5 g.), methylene chloride (800 ml.) and anhydrous sodium acetate (9.3 g.) are stirred under nitrogen at 19°. Peracetic acid (40%, 55 ml.) is added to the steroid mixture over a period of 10 minutes. The reaction mixture is stirred for 20 hours at 20°–25°. Sodium thiosulfate solution (15%, 200 ml.) is added to destroy the excess peracetic acid. The mixture is then washed with aqueous sodium bicarbonate solution (6%, 600 ml.) and a half saturated sodium chloride solution (250 ml.). The mixture is dried over magnesium sulfate and concentrated on a steam bath (80°) at atmospheric pressure while replacing the methylene chloride with SSB. The mixture is concentrated to 250 ml., SSB (500 ml.) is added, the mixture is concentrated to 425 ml., SSB (300 ml.) is added and the mixture is concentrated to 425 ml. at 65°. The mixture is then cooled to 5° and filtered. The solids are washed with SSB and dried under reduced pressure at 70° to give the title compound, 81.86 g. (98.7% chemical yield), m.p. 174°–185°; $[\alpha]_D^{25}$ +81.8° (chloroform).

EXAMPLE 2

11β-20,21-Trihydroxypregna-1,4,16-trien-3-one 21-acetate (II)

11β,21-Dihydroxy-17α,20α-epoxypregna-1,4-dien-3-one 21-acetate (I, Example 1, 20 g.) in THF (700 ml.) is stirred at 23.5°. A solution of hydrogen bromide (48%, 0.31 ml.) in THF (100 ml.) is added to the steroid mixture over a period of 38 minutes. The reaction temperature increases from 23.5° to 25.5°. during the hydrogen bromide addition. The mixture is stirred for 20 minutes and then concentrated under reduced pressure at 43° to an oil. The oil is dissolved in methylene chloride (50 ml.) at reflux. The mixture is concentrated on a steam bath at atmospheric pressure while replacing the methylene chloride with diethyl ether. When all the methylene chloride is removed and mixture is stirred at 20°-25° for 3 hours and filtered. The solids are washed with diethyl ether and dried under reduced pressure at 70° to give the title compound, 18.1 g. (90.5% chemical yield), m.p. 121.5°-135.5°; $[\alpha]_D^{25}$ +56.3° (chloroform).

EXAMPLE 3

11β,20,21-Trihydroxypregna-1,4,16-trien-3-one (III)

11β,20,21-Trihydroxypregna-1,4,16-trien-3-one 21-acetate (II, Example 2, 16.5 g.) is dissolved in acetone (170 ml.) and stirred at 20°-25°. Methanol (10 ml.) and sodium methoxide in methanol (25%, 1.25 ml.) are added and the mixture stirred for 30 minutes. Acetic acid is added to neutralize the base, the mixture is concentrated under reduced pressure with a little heat and the title compound is obtained by crystallization.

EXAMPLE 4

11β,21-Dihydroxy-17α,20α-epoxypregna-1,4-dien-3-one 21-acetate (I)

11β,21-Dihydroxypregna-1,4,17(20)-trien-3-one 21-acetate (O, 1 kg.), sodium acetate (117 g.) and methylene chloride (10 l.) are stirred at 20°. Peracetic acid (40%, 692 ml.) is added over a period of an hour and the mixture is stirred overnight at 20°. The reaction mixture is washed with anhydrous sodium thiosulfate (15%, 2.83 l.). The organic phase is then washed with aqueous sodium bicarbonate (9%, 6.5 l.) followed by a wash with an aqueous sodium chloride solution (13%, 3.1 l.). The methylene chloride is then replaced by SSB by the following procedure, the organic phase is atmospherically concentrated to about 3.1 l., SSB (4.3 l.) is added, the mixture again atmospherically concentrated to about 5.3 l., SSB (2.6 l.) is added and the mixture once again concentrated to about 5.3 l. The mixture is then cooled and filtered to obtain the title compound, 1.03 kg. (98.7% chemical yield).

EXAMPLE 5

11β,20,21-Trihydroxypregna-1,4,16-trien-3-one 21-acetate (II)

11β,21-Dihydroxy-17α,20α-epoxypregna-1,4-dien-3-one 21-acetate (I, Example 4, 1.0 kg.) in THF (33 kg.) is stirred at 25°. Hydrogen bromide (48%, 15 ml.) in THF (4.4 l.) is added over a period of one hour and the mixture is stirred for another hour at 25°-30°. The mixture is concentrated under reduced pressure to 2 l., acetone (6.3 kg.) is added and the mixture is kept at 20°-25°. The title compound may be isolated, if so desired, by the procedure of Example 2.

EXAMPLE 6

11β,20,21-Trihydroxypregna-1,4,16-trien-3-one (III)

Methanol (0.5 l.) and sodium methoxide (25% in methanol, 75 ml.) are added to 11β,20,21-trihydroxypregna-1,4,16-trien-3-one 21-acetate (II, Example 5) in acetone and the mixture is stirred for 30 minutes at 20°-25°. The title compound is obtained by the workup procedure of Example 3.

I claim:

1. A compound of the formula:

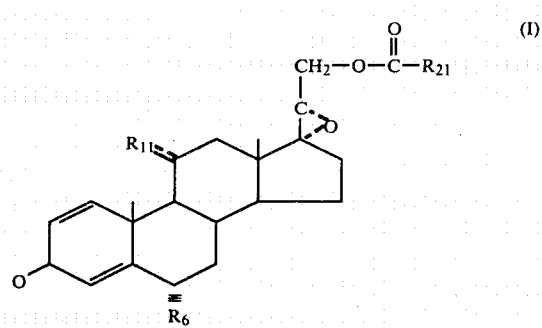

where $R_6$ is a hydrogen or fluorine atom or methyl group; $R_{11}$ is β-hydroxyl or oxo; ⸺ is a single or double bond and when $R_{11}$ is β-hydroxyl ⸺ is a single bond and when $R_{11}$ is oxo ⸺ is a double bond; $R_{21}$ is alkyl of 1 thru 3 carbon atoms, phenyl substituted with 0 thru 3 substituents which can be the same or different and are selected from the group consisting of a fluorine or chlorine atom or methyl, methoxy or nitro group.

2. A compound according to claim 1 where $R_{21}$ is methyl.

3. A compound according to claim 1 where $R_{11}$ is β-hydroxyl.

4. A compound according to claim 1 where $R_6$ is a hydrogen atom.

5. A compound according to claim 4 which is 11β,21-dihydroxy-17α,20α-epoxypregna-1,4-dien-3-one 21-acetate.

6. A process for the preparation of a compound of the formula:

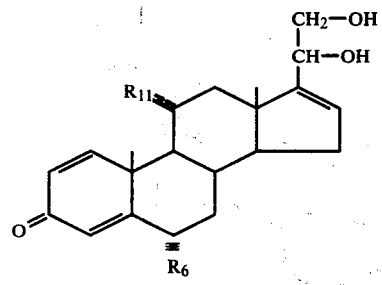

which comprises
(1) oxidizing an olefin of the formula:

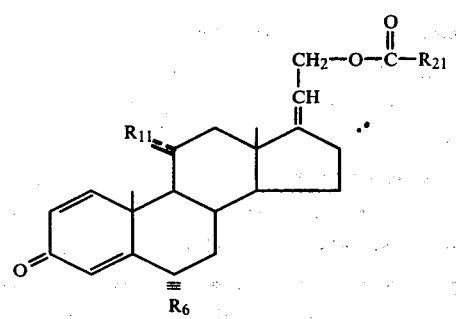

with a peracid to form an epoxide of the formula:

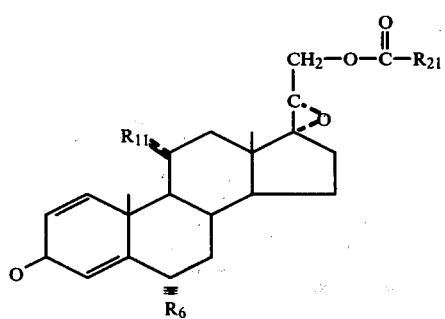

(2) opening of the epoxide ring with an acid selected from the group consisting of hydrochloric and hydrobromic to form a compound of the formula:

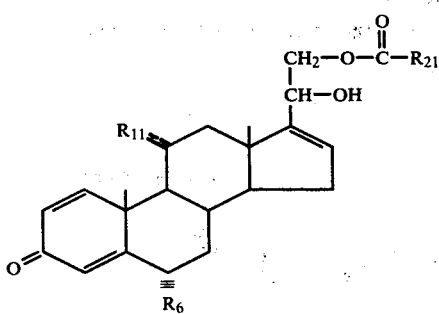

and
(3) hydrolyzing with a base, where $R_6$, $R_{11}$, $R_{21}$ and $\equiv\equiv\equiv$ are defined in claim 1.

7. A process according to claim 6 where the peracid is selected from the group consisting of peracetic, perpropionic, perbenzoic and m-chloroperbenzoic.

8. A process according to claim 6 where the base is selected from the group consisting of methoxide, ethoxide, sodium hydroxide, potassium hydroxide, sodium carbonate, potassium carbonate, sodium bicarbonate and potassium bicarbonate.

9. A process according to claim 6 where the compound of formula (0) is 11β,21-dihydroxypregna-1,4,17(20)-trien-3-one 21-acetate.

10. A process according to claim 6 where the peracid is peracetic, where the base is methoxide and where the compound of formula (0) is 11β,21-dihydroxypregna-1,4,17(20)-trien-3-one 21-acetate.

11. A process for the preparation of an epoxide of the formula:

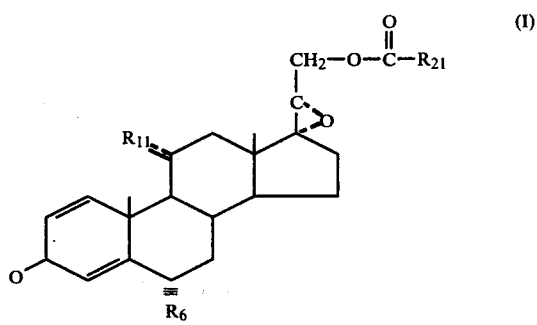

which comprises oxidizing an olefin of the formula:

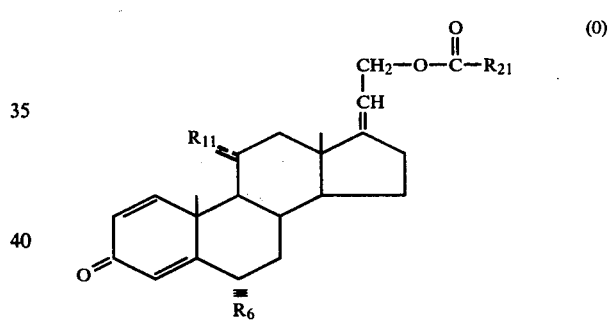

with a peracid where $R_6$, $R_{11}$, $R_{21}$ and $\equiv\equiv\equiv$ are defined in claim 1.

12. A process according to claim 11 where the peracid is selected from the group consisting of peracetic, perpropionic, perbenzoic and m-chloroperbenzoic.

13. A process according to claim 11 where the compound of the formula (0) is 11β,21-dihydroxypregna-1,4,17(20)-trien-3-one 21-acetate.

14. A process for the preparation of a compound of the formula:

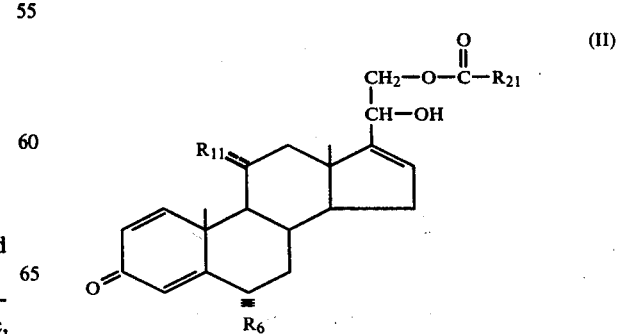

which comprises opening of the epoxide ring of an epoxide of the formula:

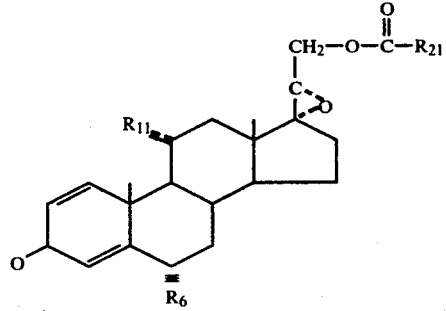

with an acid selected from the group consisting of hydrochloric and hydrobromic, where $R_6$, $R_{11}$, $R_{21}$ and ⩵ are defined in claim 1.

15. A process according to claim 14 where the acid is hydrobromic.

16. A process according to claim 14 where the compound of formula (I) is 11β,21-dihydroxy-17α,20α-epoxypregna-1,4-dien-3-one 21-acetate.

17. A process for the preparation of a compound of the formula:

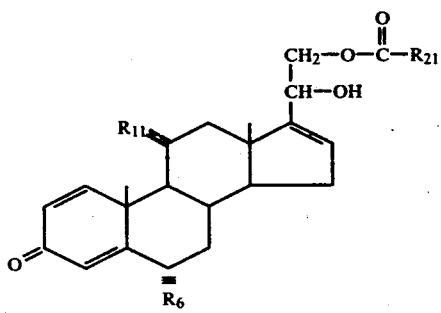

which comprises (1) oxidizing an olefin of the formula:

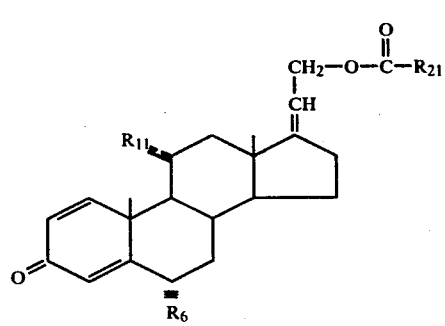

with a peracid to form a compound of the formula:

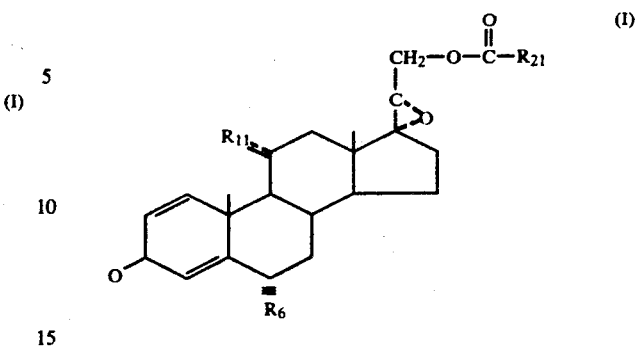

and (2) opening the epoxide ring with an acid selected from the group consisting of hydrochloric and hydrobromic, where $R_6$, $R_{11}$, $R_{21}$ and ⩵ are defined in claim 1.

18. A process according to claim 17 where the peracid is selected from the group consisting of peracetic, perproionic, perbenzoic and m-chloroperbenzoic.

19. A process according to claim 17 where the compound of formula (0) is 11β,21-dihydroxypregna-1,4,17(20)-trien-3-one 21-acetate.

20. A process for the preparation of a compound of the formula:

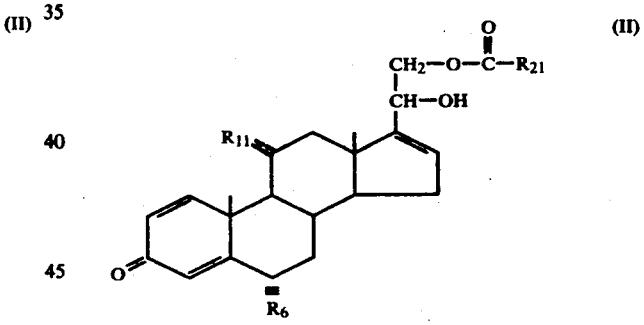

which comprises (1) opening of the epoxide ring of an epoxide of the formula:

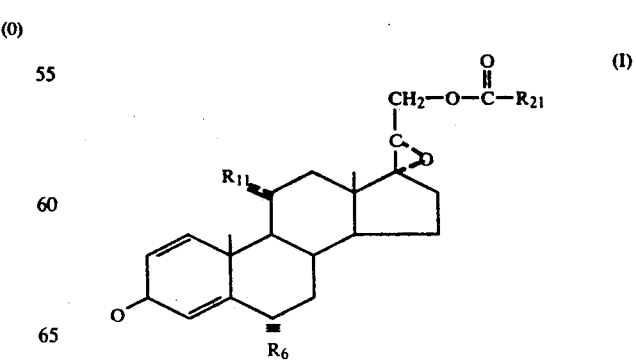

to form a compound of the formula:

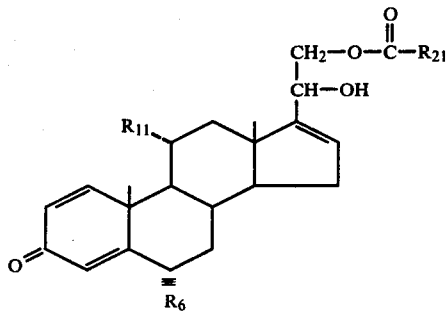

(II)

and
(2) hydrolyzing with a base, where $R_6$, $R_{11}$, $R_{21}$ and ≡≡≡ are defined in claim 1.

21. A process according to claim 17 where the acid is hydrobromic.

22. A process according to claim 17 where the base is selected from the group consisting of methoxide, ethoxide, sodium hydroxide, potassium hydroxide, sodium carbonate, potassium carbonate, sodium bicarbonate and potassium bicarbonate.

23. A process according to claim 17 where the compound of formula (I) is 11β,21-dihydroxy-17α,20α-epoxypregna-1,4-dien-3-one 21-acetate.

* * * * *

UNITED STATES PATENT AND TRADEMARK OFFICE
CERTIFICATE OF CORRECTION

PATENT NO. : 4,189,430
DATED : February 19, 1980
INVENTOR(S) : Kenneth P. Shephard It is certified that error appears in the above—identified patent and that said Letters Patent is hereby corrected as shown below:

Column 12, line 26, "perproionic" should read --perpropionic--.

Column 12, line 37, 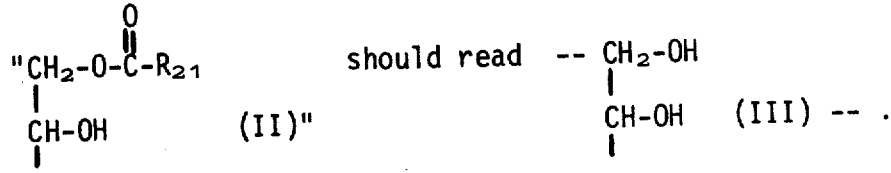 .

Column 13, line 5, "$R_{11}$  " should read -- $R_{11}$ 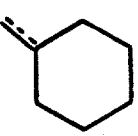 -- .

Signed and Sealed this

Eighth Day of July 1980

[SEAL]

Attest:

Attesting Officer

SIDNEY A. DIAMOND

Commissioner of Patents and Trademarks